United States Patent
Hayashi et al.

(10) Patent No.: US 6,417,361 B1
(45) Date of Patent: Jul. 9, 2002

(54) FLUORINATION AGENT AND PREPARATION AND USE OF SAME

(75) Inventors: Hidetoshi Hayashi; Hiroshi Sonoda; Ken'ichi Goto; Kouki Fukumura; Junko Naruse; Hideaki Oikawa; Teruyuki Nagata, all of Fukuoka; Takashi Shimaoka, Chiba; Tsuyoshi Yasutake, Chiba; Hideki Umetani, Chiba; Toshio Kitashima, Chiba, all of (JP)

(73) Assignee: Mitsui Chemicals, Inc., Tokyo (JP)

( * ) Notice: Subject to any disclaimer, the term of this patent is extended or adjusted under 35 U.S.C. 154(b) by 0 days.

(21) Appl. No.: 09/673,309

(22) PCT Filed: Feb. 14, 2000

(86) PCT No.: PCT/JP00/00785

§ 371 (c)(1),
(2), (4) Date: Oct. 13, 2000

(87) PCT Pub. No.: WO00/47539

PCT Pub. Date: Aug. 17, 2000

(30) Foreign Application Priority Data

| Feb. 15, 1999 | (JP) | 11-035194 |
| Jul. 7, 1999 | (JP) | 11-192503 |
| Jul. 7, 1999 | (JP) | 11-192504 |
| Jul. 7, 1999 | (JP) | 11-192505 |
| Jul. 7, 1999 | (JP) | 11-192506 |

(51) Int. Cl.$^7$ .............. A61K 31/66; C07D 239/02; C07D 211/00; C07D 33/54; C07D 325/00
(52) U.S. Cl. .............. 544/334; 544/242; 514/75; 514/114; 514/118; 546/345; 546/346; 548/335.1; 548/400; 549/29
(58) Field of Search .............. 546/345, 346; 548/335.1, 400; 549/29; 544/242, 334; 514/75, 114, 118

(56) References Cited

FOREIGN PATENT DOCUMENTS

| JP | 4124176 | * | 4/1992 |
| JP | 6-256224 | | 9/1994 |
| JP | 10-158247 | | 6/1998 |
| JP | 2000-38370 | | 2/2000 |
| JP | 2000-53650 | | 2/2000 |

OTHER PUBLICATIONS

G.A. Olah et al;"Syn.Meth. & Reac.: Pyridinium Poly–HF . . ." J. Org. Chem.,44,3872–881, Jun. 1968.*
Organic Chemistry by Morrison and Boyd, 4th Edition 1987, Allyn & Bacan, Ic,Boston, pp. 861/2,864/5,640/1,968, 1273,1278.*

*Abstract Only* Dennis G. Brown, et al., "The linear Δ H–Δ nu (sub C:O) relation for ethyl acetate adducts and its signifigance fro do nor–acceptor interations", J. Amer. Chem. Soc., 1968, vol. 90, No. 21, pp. 5706–5712.

George A. Olah, et al., "Synthetic Methods and Reactions. 63. Pyridinium Poly(hydrogen fluroide) (30% Pyridine–70% Hydrogen Fluoride): A convenient Reagent for Organic Fluorination Reactions", J. Organic Chemistry, vol. 44, No. 22, pp. 3872–3881, 1979.

Mitsunori Tsuda et al., "Hydrogen Bonding Systems Containing Hydrogen Fluoride. III.* Infrared Frequency Shifts and CNDO/2 Calculations on HF–Carbonyl Compound Complexes", Bulletin of the Chemical Society of Japan, vol. 49, No. 9, pp. 2391–2396, Sep. 1976.

* cited by examiner

Primary Examiner—Mukund J. Shah
Assistant Examiner—Sudhaker B. Patel
(74) Attorney, Agent, or Firm—Burns, Doane, Swecker & Mathis, LLP

(57) ABSTRACT

The invention disclose a hydrogen fluoride containing composition comprising hydrogen fluoride and a compound which is liquid in the standard state (25° C., 1 atmosphere) and has a boiling point of 120° C. or more and pka of 12 or more at 25° C., and use of the composition for a fluorination agent. The compound which can be preferably used is represented by the formula (1):

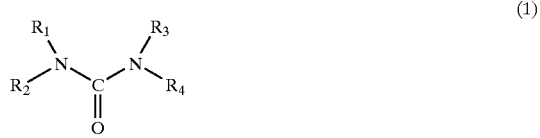

(1)

wherein $R_1$ to $R^4$ are a substituted or unsubstituted alkyl or aryl group and can be the same or different, and $R_1$ or $R_2$ or $R_3$ and $R_4$ can bond to form a ring having a nitrogen atom or a nitrogen atom and other hetero atom, or $R_1$ and $R_3$ can bond to form a ring having a nitrogen atom or a nitrogen atom and other hetero atom. The fluorination agent of the invention exerts effect with a similar reaction mechanism to hydrogen fluoride, can be applied to the halogen exchange reaction of a halogen containing organic compound, and can produce a fluorine containing compound with safety and ease without specific equipment or technique.

24 Claims, No Drawings

FLUORINATION AGENT AND PREPARATION AND USE OF SAME

TECHNICAL FIELD

The present invention relates to a novel hydrogen fluoride containing composition, application of the composition to a fluorination agent, and preparation process of a fluorine-containing compound by using the composition.

BACKGROUND ART

Many processes have so far been known on the halogenation reaction of an organic compound. Compounds which can be used for a halogenation agent include hydrogen halide, phosphorous halide, sulfur halide and halogen simple body. However, these compounds are very corrosive and toxic, and many of these compounds require special equipment and technique. Accordingly, the investigation for developing a halogenation agent has been still continued in view of handling, safety and reactivity.

The fluorination agents which have been conventionally used in fluorinating reactions include fluorine, anhydrous hydrogen fluoride and sulfur tetrafluoride. However, these conventional fluorination agents are difficult to handle because of toxicity, corrosivity and danger of explosion in reaction and thus special equipment and technique are required. It is also a problem that required selectivity of a fluorine bond in the reaction is poor. On the other hand, development of new products utilizing fluorine compounds has been carried out in various fields such as functional materials and physiologically active substances. Keeping pace with such trend, various fluorination agents are recently in a development stage.

Anhydrous hydrogen fluoride (HF) is widely used in a great amount as a basic fluorine source in the fluorine chemical industry. However, it is difficult to handle because of a low boiling point (b.p. 19.5° C.) and strong toxicity and corrosivity. When using hydrogen fluoride, the equipment must have acid proof property and pressure tight structure. Further, specific technique is required, and thus it is very difficult to use in industry.

In order to solve these problems, a complex of HF and Lewis base has been developed as a fluorination agent which is easy to handle and exhibits reaction mechanism similar to hydrogen fluoride (hereinafter referred to as HF-like fluorination agent). For example, pyridine-70 wt % (HF)n (Olah agent) has been reported in J. Org. Chem., 44, 3872 (1979) and triethylamine-3HF has been described in Aldrichimica Acta., 28, 31 (1995). However, these fluorination agents are difficult to control in the preparation step due to a considerably exothermic reaction. Further, it is difficult to use in industry in view of recovery and reuse.

HF is an important fluorine source in the fluorine chemical industry. Consequently, the development of an improved HF-like fluorination agent is very significant in the area of fluorine chemistry in order to overcome handling problems and to make the application simple in broad area.

The subject of the present invention is to provide hydrogen fluoride, which is a suitable fluorination agent for the preparation of a fluorine- containing compound, in the form of a fluorination agent which is easy to handle and can be conveniently used.

DISCLOSURE OF THE INVENTION

As a result of an intensive investigation in order to solve these subjects, the present inventors have found that a hydrogen fluoride containing composition obtained by adding hydrogen fluoride to a compound which is liquid in the standard state (25° C., 1 atmosphere) and has a boiling point of 120° C. or more, preferably to the compound which is liquid in the standard state (25° C., 1 atmosphere) and has a boiling point of 120° C. or more and pka of 12 or more at 25° C., the composition is easy to handle and useful as a novel fluorination agent having fluorinating effect similar to hydrogen fluoride, and further found that the fluorinating reaction can progress in high safety with ease without requiring special equipment and technique. Thus the present invention has been completed.

That is, the aspect of the present invention is a hydrogen fluoride containing composition obtained by adding hydrogen fluoride to a compound which is liquid in the standard state (25° C., 1 atmosphere) and has a boiling point of 120° C. or more, preferably to the compound which is liquid in the standard state (25° C., 1 atmosphere) and has a boiling point of 120° C. or more and pka of 12 or more at 25° C., use of said composition for fluorination agent and a preparation process of a fluorine containing compound by using said composition for a fluorination agent.

The invention will be more specifically illustrated in items (1) to (7) below.

(1) A hydrogen fluoride containing composition comprising hydrogen fluoride and a compound being liquid in the standard state (25° C., 1 atmosphere) and having a boiling point of 120° C. or more, and a fluorination agent comprising said composition.

(2) A hydrogen fluoride containing composition comprising hydrogen fluoride and a compound being liquid in the standard state (25° C., 1 atmosphere) and having a boiling point of 120° C. or more and pka of 12 or more at 25° C., and a fluorination agent comprising said composition.

(3) A hydrogen fluoride containing composition comprising 7 mol or more of hydrogen fluoride for 1 mol of a compound being liquid in the standard state (25° C., 1 atmosphere) and having a boiling point of 120° C. or more and pka of 12 or more at 25° C., and a fluorination agent comprise said composition.

(4) A hydrogen fluoride containing composition and a fluorination agent comprising said composition in items (1) to (3) wherein (I) the compound is represented by the formula (1):

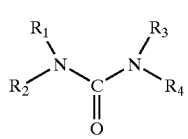

wherein $R_1$ to $R_4$ are a substituted or unsubstituted alkyl or aryl group and can be the same or different, and $R_1$ and $R_2$ or $R_3$ and $R_4$ can bond to form a ring having a nitrogen atom or a nitrogen atom and other hetero atom, or $R_1$ and $R_3$ can bond to form a ring having a nitrogen atom or a nitrogen atom and other hetero atom, ② the compound is represented by the formula (6):

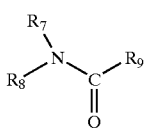 (6)

wherein $R_7$ and $R_8$ are a substituted or unsubstituted alkyl or aryl group, $R_9$ is a hydrogen atom or a substituted or unsubstituted alkyl or aryl group, these groups can be the same or different, and $R_7$ and $R_9$ can bond to form cyclic amide, ③ the compound is represented by the formula (10):

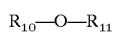 (10)

wherein $R_{10}$ and $R_{11}$, are a substituted or unsubstituted alkyl or aryl group and can be the same or different, and $R_{10}$ and $R_{11}$, can bond to form cyclic ether, ④ the compound is represented by the formula (12):

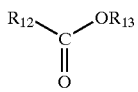 (12)

wherein $R_{12}$ and $R_{13}$ are a substituted or unsubstituted alkyl or aryl group and can be the same or different, and $R_{12}$ and $R_{13}$, can bond to form cyclic ester or ⑤ the compound has the formula (14):

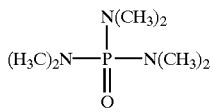 (14)

(5) A hydrogen fluoride containing composition and a fluorination agent comprising the composition wherein the compound represented by the formula (1) is: ⑥ a compound represented by the formula (2):

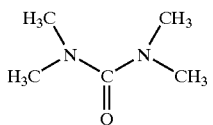 (2)

⑦ a compound represented by the formula (3):

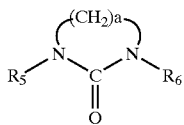 (3)

wherein a is an integer of 2 or 3, and R and $R_6$ are a substituted or unsubstituted alkyl group having 1 to 6 carbon atoms and can be the same or different, and the compound represented by the formula (3) is a compound having the formula (4):

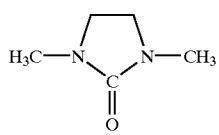 (4)

or the formula (5):

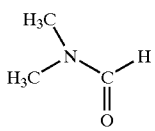 (5)

and further ⑧ the composition wherein the compound represented by the formula ⑥ is a compound having the formula (7):

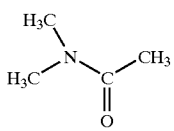 (7)

the formula (8):

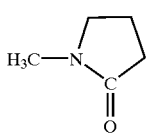 (8)

or the formula (9):

 (9)

⑨ the composition wherein the compound represented by the formula (10) is a compound having the formula (11):

$(CH_3OCH_2CH_2)_2O$ (11)

or ⑩ the composition wherein the compound represented by the formula (12) is a compound having the formula (13):

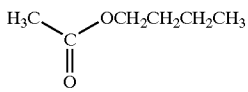 (13)

As illustrated above, the invention is each composition above and the use of the composition for a fluorination agent.

(6) A preparation process comprising reacting the fluorination agent with a compound represented by the formula (15):

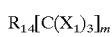 (15)

wherein $R_{14}$ is a substituted or unsubstituted alkyl, alkoxy, aryl or aryloxy group, $X_1$ is a hydrogen, fluorine, chlorine, bromine or iodine atom and can be the same or different except three X, are not simultaneously hydrogen or fluorine atoms and three $X_1$ do not consist of hydrogen and fluorine atoms alone, and m is an integer of 1 to 6, to obtain a fluorine compound represented by the formula (16):

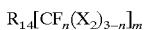  (16)

wherein $R_{14}$ is a substituted or unsubstituted alkyl, alkoxy, aryl or aryloxy group, $X_2$ is a hydrogen, chlorine, bromine or iodine atom and can be the same or different, and n is an integer of 1 to 3 and m is an integer of 1 to 6.

(7) A preparation process comprising reacting, as a compound represented by the formula (16), a heterocyclic aromatic compound represented by the formula (17):

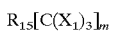  (17)

wherein $R_{15}$ is a substituted or unsubstituted heterocyclic aromatic group, and $X_1$ is a hydrogen, fluorine, chlorine, bromine or iodine atom and can be the same or different except three $X_1$ are not simultaneously hydrogen or fluorine atoms and three $X_1$ do not consist of hydrogen and fluorine atoms alone, and m is an integer of 1 to 9, to obtain a fluorine containing heterocyclic aromatic compound represented by the formula (18):

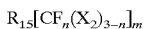  (18)

wherein $R_{15}$ is a substituted or unsubstituted heterocyclic aromatic group, and $X_2$ is a hydrogen, chlorine, fluorine, bromine or iodine atom and can be the same or different, and n is an integer of 1 to 3 and m is an integer of 1 to 9.

In the preparation process, ① the heterocyclic aromatic compound represented by the formula (17) is cyclic compound having 1 to 4 elements of one or more species selected from the group consisting of nitrogen, oxygen and sulfur, for example, a heterocyclic aromatic compound having a ring selected from furan, thiophene, pyrrole, pyrazole, imidazole, isoxazole, thioazole, thiadiazole, pyridine, pyridazine, pyrimidine, pyrazine, triazine, benzofuran, indole, thianaphthane, benzimidazole, benzoxazole, benzothiazole, benzotriazole, purine, quinoline, isoquinoline, cinnoline, quinoxaline, dibenzothiophene, acridine, and phenanthroline.

Further, ② the heterocyclic aromatic compound represented by the formula (17) is a compound represented by the formula (19):

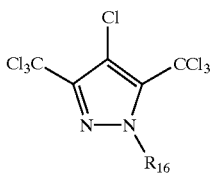  (19)

wherein $R_{16}$ is a hydrogen atom or alkyl group having 1 to 4 carbon atoms, in particular, 4-chloro-3,5-bis(trichloromethyl)pyrozole having the formula (20):

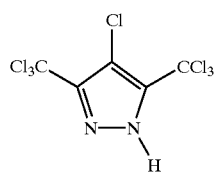  (20)

or, ③ the heterocylic aromatic compound is a compound represented by the formula (21):

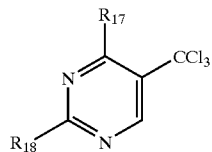  (21)

wherein $R_{17}$ and $R_{18}$ are a hydrogen, chlorine or fluorine atom, a hydroxy, alkyl having 1 to 4 carbon atoms, alkoxy, aryl or aryloxy group and can be the same or different, in particular, 2,4-dichloro-5-trichloromethylpyridine having the formula (22):

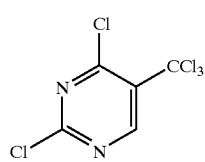  (22)

And further, ④ the heterocyclic aromatic compound is a compound represented by the formula (23):

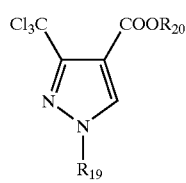  (23)

wherein $R_{19}$ and $R_{20}$ are a hydrogen atom or an alkyl group having 1 to 4 carbon atoms and can be the same or different, and particularly is ethyl 1-methyl-3-trichloromethylpyrazole-4-carboxylate having the formula (24):

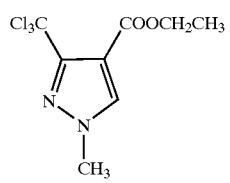  (24)

The hydrogen fluoride containing composition of the invention can be used for a fluorination agent having a reaction mechanism similar to hydrogen fluoride.

Further, the composition agent can be used not only for a fluorination agent, but also for an acid catalyst. When using for a fluorination agent, the composition preferably contains 7 mole or more hydrogen fluoride for 1 mole of the above compound.

The fluorination agent can be recovered and reused with ease after finishing the reaction and thus provides increased economy.

BEST MODE FOR CARRYING OUT THE INVENTION

The hydrogen fluoride containing composition of the invention is a composition comprising hydrogen fluoride and a below described compound.

That is, the compound is (a) liquid in the standard state (25° C., 1 atmosphere) and is required to have (b) a boiling point of 120° C. or more. More preferably, the compound is liquid in the standard state (25° C., 1 atmosphere), has a boiling point of 120° C. or more, and additionally has (c) pka of 12 or more at 25° C.

Hydrogen fluoride which can be used is an anhydrous grade.

In the hydrogen fluoride containing composition of the invention, (i) the above compound and hydrogen fluoride can form salt or complex, (ii) Hydrogen fluoride can coordinate to a free electron pair in the compound molecule. (iii) Hydrogen fluoride can form straight or branched hydrogen bonding with partial inclusion of the compound molecule. Or (iv) Hydrogen fluoride can dissolve in the compound to form a simple mixture.

The properties of the compound which consist the hydrogen fluoride containing composition in the invention, that is, liquid state in the standard state (25° C., 1 atmosphere), boiling point of 120° C. or more and preferably pka of 12 or more at 25° C., are specified in view of reaction temperature and reactivity when used for a fluorination agent.

The compounds constituting the hydrogen fluoride containing composition include various compounds having the above specified properties, preferably compounds selected from the group consisting of those represented by the formulas (1), (6), (10) and (12) and the formula (14) below.

A compound represented by the formula (1):

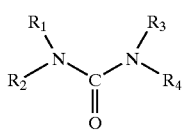

(1)

wherein $R_1$ to $R_4$ are a substituted or unsubstituted alkyl or aryl group and can be the same or different, $R_1$ and $R_2$ or $R_3$ and $R_4$ can bond to form a ring having a nitrogen atom or a nitrogen atom and other hetero atom, and $R_1$ and $R_3$ can bond to form a ring having a nitrogen atom or a nitrogen atom and other hetero atom.

A compound represented by the formula (6):

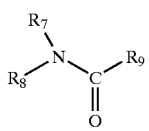

(6)

wherein $R_7$ and $R_8$ are a substituted or unsubstituted alkyl or aryl group, $R_9$ is hydrogen atom, or a substituted or unsubstituted alkyl or aryl group and $R_7$, $R_8$ and $R_9$ can be the same or different, and $R_7$ and $R_9$ can bond to form cyclic amide.

A compound represented by the formula (10):

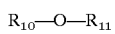

(10)

wherein $R_{10}$ and $R_{11}$ are a substituted or unsubstituted alkyl or aryl group and can be the same or different, and $R_{10}$ and $R_{11}$ can bond to form a cyclic ether.

A compound represented by the formula (12):

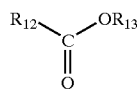

(12)

wherein $R_{12}$ and $R_{13}$ are a substituted or unsubstituted alkyl or aryl group and can be the same or different, and $R_{12}$ and $R_{13}$ can bond to form a cyclic ester.

A compound having the formula (14):

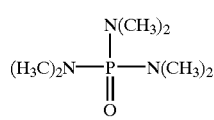

(14)

Each compound will be illustrated herein after.

(i) In the compound represented by the formula (1), $R_1$ to $R_4$ are a substituted or unsubstituted alkyl or aryl group, preferably alkyl or aryl group having 1 to 6 carbon atoms and can be the same or different, and the alkyl group having can be straight or branched.

The alkyl and aryl groups include, for example, a methyl, ethyl, n-propyl, isopropyl, n-butyl, isobutyl, t-butyl, n-pentyl, n-hexyl, cyclohexyl and phenyl group.

Further, $R_1$ and $R_2$ or $R_3$ and $R_4$ can respectively bond to form a heterocyclic ring having a nitrogen atom and 3 to 5 carbon atoms, which includes, for example, a pyrrolidine ring and piperidine ring.

Moreover, $R_1$ and $R_3$ can bond to form a heterocyclic, 5 or 6 membered ring having two nitrogen atoms as represented by the formula (3):

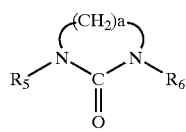

(3)

Such a ring includes, for example, an imidazolidinone ring and pyrimidinone ring.

Specific compounds which can be represented by the formula (1) and formula (3) include, for example, 1,1,3,3-tetramethylurea, 1,3-dimethyl-2-imidazolidinone, 1,3-diethylimidazolidinone, 1,3-di(n-propyl)-2-imidazolidinone, 1,3-di(n-butyl)-2-imidazolidinone, N,N'-dimethylpropyleneurea, N,N'-diethylpropyleneurea, N,N'-di(n-propyl)propyleneurea and N,N'-di(n-butyl)propyleneurea.

The compounds represented by the formula (1) is preferably 1,1,3,3-tetramethylurea having the formula (2)

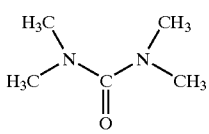

(2)

In the compounds represented by the formula (3):

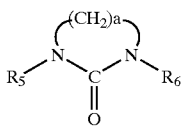

(3)

$R_5$ and $R_6$ are a substituted or unsubstituted alkyl group having 1 to 6 carbon atoms and can be the same or different, and include, for example, a methyl, ethyl, n-propyl, isopropyl, n-butyl, isobutyl, t-butyl, n-pentyl, n-hexyl and cyclohexyl group.

The compound represented by the formula (3) is preferably 1,3-dimethyl-2-imidazolidinone having the formula (4):

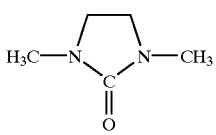

(4)

or N,N'-dimethylpropyleneurea having the formula (5):

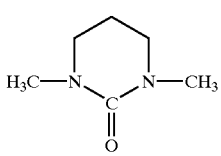

(5)

Particularly preferred compound represented by the formula (1) is 1,3-dimethyl-2-imidazolidinone.

(ii) In the compounds represented by the formula (6):

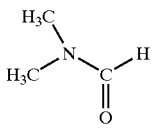

(7)

$R_7$ and $R_8$ are a substituted or unsubstituted alkyl or aryl group, $R_9$ is a hydrogen atom or a substituted alkyl or aryl group, and $R_7$, $R_8$ and $R_9$ can be the same or different. The alkyl or aryl group includes, for example, a methyl, ethyl, n-propyl, isopropyl, n-butyl, isobutyl, t-butyl, n-pentyl, n-hexyl, cyclohexyl and phenyl group. $R_7$ and $R_9$ can bond to form cyclic amide.

N,N-diethylformamide, N,N-dimethylacetoamide having the formula (8):

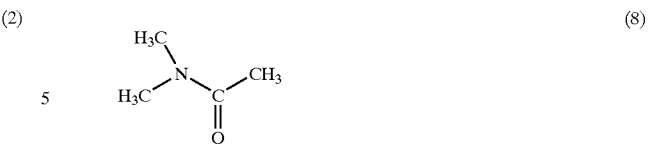

(8)

and 1-methyl-2-pyrrolidone having the formula (9):

(9)

(iii) In the compound represented by the formula (10):

$R_{10}$ and $R_{11}$ are a substituted or unsubstituted alkyl, alkoxyalkyl or aryl group and can be the same or different. $R_{10}$ and $R_{11}$ include, for example, an alkyl group having more than 4 carbon atoms or phenyl group, and can bond to form cyclic ether having 1 to 3 oxygen atoms.

Specific compounds represented by the formula (10) include n-butyl ether, n-hexyl ether, anisole, phenetole, butyl phenyl ether, amyl phenyl ether, methoxytoluene, benzyl ethyl ether, diphenyl ether, dibenzyl ether, 1,2-diethoxyethane, 1,2-dibutoxyethane, diethylene glycol dimethyl ether, diethylene glycol diethyl ether, and diethylene glycol dibutyl ether, preferably, diethylene glycol dimethyl ether having the formula (11):

$$(CH_3OCH_2CH_2)_2O \quad (11)$$

(iv) In the compound represented by the formula (12):

(12)

$R_{12}$ and $R_{13}$ are a substituted or unsubstituted alkyl or aryl group and can be the same or different. Representative alkyl or aryl groups include, for example, a methyl, ethyl, n-propyl, isopropyl, n-butyl, isobutyl, t-butyl, npentyl, n-hexyl, cyclohexyl, and phenyl group.

$R_{12}$ and $R_{13}$ can bond to form cyclic ester.

Specific compounds represented by the formula (12) include n-butyl acetate, n-pentyl acetate, isopentyl acetate, cyclohexyl acetate, benzyl acetate, butyl propionate, isopentyl propionate, methyl benzoate, dimethyl phthalate, and γ-butyrolactone, preferably n-butyl acetate having the formula (13):

(13)

(v) The compound having the formula (14) is hexamethylphosphoramide.

As to the hydrogen fluoride containing composition of the invention, hydrogen fluoride is preferably in such an amount that the composition does not release hydrogen fluoride out of the system in the standard state (25° C., 1 atmosphere).

The amount of hydrogen fluoride depends upon species, property and temperature of the compound which constitutes the hydrogen fluoride containing composition. The molar number of hydrogen fluoride per mole of the compound which constitutes the hydrogen fluoride containing composition is generally 2 to 25 moles, preferably 7 to 20 moles, more preferably 10 to 18 moles.

When the compound constituting the hydrogen fluoride containing composition forms salt or complex with hydrogen fluoride, it is liable to form a mixture of salt or complex which differs in the coordination number, for example, 1 HF salt or 2 HF salt of the compound. The term "the molar number of hydrogen fluoride per mole of the hydrogen fluoride containing composition" is referred to as the value obtained by dividing the molar number of the total hydrogen fluoride with the molar number of the compound, and is defined to indicate the average molar number of hydrogen fluoride for 1 mole of the compound which constitutes the hydrogen fluoride containing composition.

The hydrogen fluoride containing composition can be prepared by adding anhydrous hydrogen fluoride to the compound for constituting the hydrogen fluoride containing composition.

Anhydrous hydrogen fluoride can be added in the liquid state or can be blown through the compound in the gaseous state.

Anhydrous hydrogen fluoride is added at temperature of −20 to 20° C., preferably −10 to 10° C., more preferably, 0 to 5° C.

Anhydrous hydrogen fluoride can be added at velocity which inhibits short pass of anhydrous hydrogen fluoride and does not accompany violent exotherm. For example, when the amount of anhydrous hydrogen fluoride to be added is approximately 100 g for 50 g of the compound, the addition velocity is usually 1.5 to 3.0 g/min,, preferably 2.0 to 2.5 g/min. However, at the initiation time of anhydrous hydrogen fluoride addition, exotherm becomes great and thus slow down of the addition velocity is sometimes required.

The hydrogen fluoride containing composition of the invention is stirred at desired temperature after blowing anhydrous hydrogen fluoride, excessive hydrogen fluoride is released out of the reaction system to bring hydrogen fluoride content into equibilium state, and thus hydrogen content can be controlled to a desired level.

The hydrogen fluoride containing composition of the invention can be stored preferably in a hydrogen fluoride resistant container, more preferably, in a hydrogen fluoride resistant pressure vessel, and can be used for a fluorination agent or catalyst of various reactions.

The present invention uses the above hydrogen fluoride containing composition for a fluorination agent.

The fluorination agent of the invention respectively corresponds to the above hydrogen fluoride containing composition, that is, for example:

(1) A fluorination agent comprising hydrogen fluoride and a compound which is liquid in the standard state(25° C., 1 atmosphere) and has a boiling point of 120° C. or more.

(2) A fluorination agent comprising hydrogen fluoride and a compound which is liquid in the standard state (25° C., 1 atmosphere) and has a boiling point of 120° C. or more and pka of 12 or more at 25° C.

(3) A fluorination agent comprising hydrogen fluoride and a compound which is liquid in the standard state (25° C., 1 atmosphere) and has a boiling point of 120° C. or more and pka of 12 or more at 25° C., and having a hydrogen fluoride molar number of 7 or more for 1 mole of the compound.

Similarly, the hydrogen fluoride containing composition having other embodiment of the invention is respectively defined as a fluorination agent.

In the invention, on the basis of the molar ratio of hydrogen fluoride to the compound which constitutes the hydrogen fluoride containing composition, the fluorination agent is indicated, for example, by DMI.nHF when the compound is 1,3-dimethylimidazolidinone (DMI).

The fluorination agent of the invention can be applied not only to the reaction wherein hydrogen fluoride is effective as a fluorination agent, but to other various fluorinating reactions, and is useful for fluorination of a fluoro-organic compound, particularly for a fluorination agent in the fluorinating reaction illustrated below.

The reaction is a preparation process of a fluorine containing compound by way of a halogen exchange reaction using the halogenation agent of the invention, that is, a halogen exchange reaction of a halogen containing aliphatic, aromatic or heterocyclic aromatic compound.

That is, a halogenide represented by the formula (15):

$$R_{14}[C(X_1)_3]_m \qquad (15)$$

wherein $R_{14}$, is a substituted or unsubstituted alkyl, alkoxy, aryl or aryloxy group, and $X_1$ is a hydrogen, fluorine, chlorine, bromine or iodine atom and can be the same or different except three $X_1$ are not simultaneously hydrogen or fluorine atoms and three $X_1$ do not consist of hydrogen and fluorine atoms alone, and m is an integer of 1 to 6, is reacted with the hydrogenation agent of the invention to prepare a fluorine compound represented by the formula (16):

$$R_{14}[CF_n(X_2)_{3-n}]_m \qquad (16)$$

wherein $R_{14}$, is a substituted or unsubstituted alkyl, alkoxy, aryl or aryloxy , group, and $X_2$ is a hydrogen, chlorine, bromine or iodine atom and can be the same or different, and n is an integer of 1 to 3 and m is an integer of 1 to 6.

Representative compounds represented by the formula (15) includes, for example, 1,1,1,3-tetrachloro-3-methylbutane, benzyl chloride, benzoyl chloride, benzotrichloride, (chlorodifluoromethyl)benzene, (dichlorofluoromethyl)benzene, 2-chlorobenzotrichloride, 4-chlorobenzotrichloride, dichlorobenzotrichloride, 2-fluorobenzotrichloride, 2-nitrobenzotrichloride, 3-nitrobenzotrichloride, 4-nitrobenzotrichloride, (trichloromethyl)benzene, 1,3-bis(trichloromethyl)benzene and 1,4-bis(trichloromethyl)benzene. However, these compounds do not limit the scope of the invention.

These compounds represented by the formula (15) can be respectively converted to the corresponding fluorine compounds represented by the formula (16).

A halogenated heterocyclic aromatic compounds represented by the formula (17):

$$R_{15}[C(X_1)_3]_m \qquad (17)$$

wherein $R_{15}$, is a substituted or unsubstituted heterocyclic aromatic group, and $X_1$ is a hydrogen, fluorine, chlorine, bromine or iodine atom and can be the same or different except three $X_1$ are not simultaneously a hydrogen or fluorine atom and three $X_1$ do not consist of a hydrogen or fluorine atom alone, and m is an integer of 1 to 9, reacts with the fluorination agent of the invention to prepare a fluorine containing heterocyclic aromatic compound represented by the formula (18):

$$R_{15}[CF_n(X_2)_{3-n}]_m \qquad (18)$$

wherein $R_{15}$, is a substituted or unsubstituted heterocyclic aromatic group, and $X_2$ is a hydrogen, chlorine, chlorine, bromine or iodine atom and can be the same or different, and n is an integer 1 to 3 and m is an integer of 1 to 9.

The term "heterocyclic aromatic compound" in the invention is referred to as a heterocyclic compound having 1 to 4 atoms of one or more species of element selected from the group consisting of nitrogen, oxygen and sulfur.

In the formulas (17) and (18), m is an integer of 1 to 9 and is the number of trihalomethyl group located as a side chain.

The number of configuration is restricted due to the structure of a common heterocyclic compound and thus the upper limit is appropriately 9.

Generally, the velocity of a halogen exchange reaction is liable to reduce with increase in the number of m.

The heterocyclic aromatic compounds represented by the formula (17) preferably have a ring selected from furan, thiophene, pyrrole, pyrazole, imidazole, isoxazole, thiazole, thiodiazole, pyridine, pyridazine, pyrimidine, pyrazine, triazine, benzofuran, indole, thionaphthene, benzimidazole, benzoxazole, benzothiazole, benzotriazole, purine, quinoline, isoquinoline, cinnoline, quinoxaline, dibenzothiophene, acridine and phenanthroline.

The compounds represented by the formula (17) will be exemplified below. However, these compounds are not to be construed to limit the scope of the invention.

Exemplary compounds are as follows.

Oxygen containing heterocyclic aromatic compounds include 3-trichloromethylfuran, 3-tribromomethylfuran, 2,3-bis(trichloromethyl)benzofuran and 2,3-bis(tribromomethyl)benzofuran.

Sulfur containing heterocyclic aromatic compounds include 2-trichloromethylthiophene, 3-trichloromethylthiophene, 2,3-bis(trichloromethyl)thiophene, 2,5-bis(trichloromethyl)thiophene, 3,4-bis(trichloromethyl)thiophene, 2-tribromomethylthiophene, 3-triboromomethylthiophene, 2,3-bis(tribromomethyl)thiophene, 2,5-bis(tribromomethyl)thiophene, 3,4-bis(tribromomethyl)thiophene, 2-trichloromethylthionaphthene, 2-trichloromethylthionaphthene, 4,6-bis(trichloromethyl)dibenzothiophene and 4,6-bis(tribromomethyl)dibenzothiophene.

Nitrogen containing heterocyclic aromatic compounds include 2-trichloromethylpyrrole, 2-tribromomethylpyrrole, 4-chloro-3-trichloromethylpyrazole, 4-chloro-3,5-bis(trichloromethyl)pyrazole, 4-chloro-3-tribromomethylpyrazole, 4-chloro-3,5-bis(tribromomethyl)pyrazole, 1-methyl-3-trichloromethylpyrazole-4-carboxylate, 1,2-bis(trichloromethyl)imidazole, 1,3-bis(trichloromethyl)imidazole, 1,5-bis(trichloromethyl)imidazole, 2,5-bis(trichloromethyl)imidazole, 4,5-bis(trichloromethyl)imidazole, 1,2,5-tris(trichloromethyl)imidazole, 2,3,4-tris(trichloromethyl)imidazole, 1,2-bis(tribromomethyl)lmidazole, 1,3-bis(tribromomethyl)imidazole, 1,5-bis(tribromomethyl)imidazole, 2,5-bis(tribromomethyl)imidazole, 4,5-bis(tribromomethyl)imidazole, 1,2,5-tris(tribromomethyl)imidazole, 2,3,4-tris(tribromomethyl)imidazole, 2-trichloromethylpyridine, 3-trichloromethylpyridine, 4-trichloromethylpyridine, 2,3-2,5-bis(trichloromethyl)pyridine, 2,6-bis (trichloromethyl)pyridine, 3,5-bis(trichloromethyl)pyridine, 2-tribromomethylpyridine, 3-tribromomethylpyridine, 4-tribromomethylpyridine, 2,3-2,5-bis(tribromomethyl)pyridine, 2,6-bis(tribromomethyl)pyridine, 3,5-bis(tribromomethyl)pyridine, 3-trichloromethylpyridazine, 3-tribromomethylpyridazine, 4-trichloromethylpyridazine, 4-tribromomethylpyridazine, 2,4-bis(trichloromethyl)pyrimidine, 2,6-bis(trichloromethyl)pyrimidine, 2,4-bis,(tribromomethyl)pyrimidine, 2,6-bis(tribromomethyl)pyrimidine, 2,4-dichloro-5-trichloromethylpyridine, 2-trichloromethylpyrazine, 2-tribromomethylpyrazine, 1,3,5-trisbis(trichloromethyl)triazine, 1,3,5-trisbis(tribromomethyl)triazine, 4-trichloromethylindole, 5-trichloromethylindole, 4-tribromomethylindole, 5-tribromomethylindole, 2-trichloromethylbenzimidazole, 2-tribromomethylbenzimidazole, 5-trichloromethyl-1H-benzotriazole, 5-tribromomethyl-1H-benzotriazole, 6-trichloromethylpurine, 6-tribromomethylpurine, 3-trichloromethylquinoline, 4-trichloromethylquinoline, 3-tribromethylquinoline, 4-tribromomethylquinoline, 3-trichloromethylisoquinoline, 3-tribromomethylisoquinoline, 4-trichloromethylcinnoline, 4-tribromomethylcinnoline, 2-trichloromethylquinoxaline, 2-tribromomethylquinoxaline, 5-trichloromethylquinoxaline, 5-tribromomethylquinoxaline, 9-trichloromethylacridine, 9-tribromomethylacridine, 4-trichloromethyl-1,10-phenanthroline, 4-tribromomethyl-1,10-phenanthroline, 5-trichloromethyl-1,10-phenanthroline, and 5-tribromomethyl-1,10-phenanthroline.

Oxygen and nitrogen containing heterocyclic aromatic compounds include 3,5-bis(trichloromethyl)isoxazole, 3,5-bis(tribromomethyl)isoxazole, 2-trichloromethylbenzoxazole, and 2-tribromomethylbenzoxazole.

Sulfur and nitrogen containing heterocyclic aromatic compounds include 4,5-bis(trichloromethyl)thiazole, 4,5-bis(tribromomethyl)thiazole, 5-trichloromethylthiodiazole, 5-tribromomethylthiodiazole, 2-trichloromethylbenzothiazole, and 2-tribromomethylbenzothiazole.

Compounds which can be favorably fluorinated in particular are those represented by the formula (19):

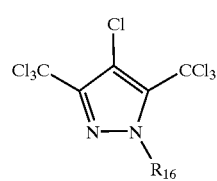

(19)

wherein $R_{16}$ is a hydrogen atom or an alkyl group having 1 to 4 carbon atoms, for example, 4-chloro-3,5-bis(trichloromethyl)pyrazole having the formula (20):

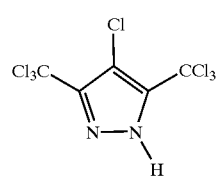

(20)

by the formula (21):

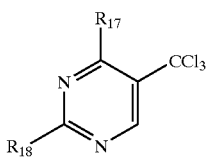

(21)

wherein $R_{17}$ and $R_{18}$ are a hydrogen, chlorine or fluorine atom or a hydroxyl, alkyl or alkoxy group having 1 to 4 carbon atoms, aryl or aryloxy group, and can be the same or different, for example, 2,4-dichloro-5-trichloromethylpyrimidine having the formula (22):

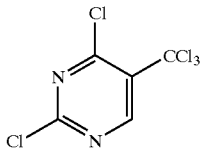

(22)

and further by the formula (23):

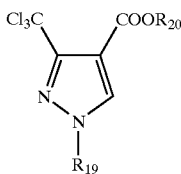

(23)

wherein $R_{19}$ and $R_{20}$ are a hydrogen atom or alkyl group having 1 to 4 carbon atoms and can be the same or different, for example, ethyl 1-methyl-3-trichloromethylpyrazole-4-carboxylate having the formula (24):

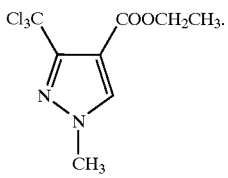

(24)

As illustrated above, these compounds represented by the formula (17) can be respectively converted to the corresponding flourine compounds represented by the formula (18).

The fluorination agent is used in an amount containing usually 1 equivalent or more, preferably 2 to 10 equivalents of hydrogen fluoride for 1 halogen atom to be substituted.

When a solvent is used for the reaction, no particular restriction is imposed upon the solvent as long as the solvent does not form complex by interaction with hydrogen fluoride. Preferred solvent includes acetonitrile, dichloromethane and ethylene dichloride.

The reaction temperature depends upon the solvent and reactivity of substrate, and is in the range of preferably −40 to 160° C., were preferably −20 to 150° C. in view of reaction velocity and stability of the fluorination agent.

The halogen exchange reaction of the compounds represented by the formulas (15) and (17) is a consecutive reaction.

The number of fluorine to be introduced can be controlled to 1 to 3 by adjusting the reaction temperature, pressure and hydrogen fluoride content of the fluorination agent.

In the fluorination reaction of the invention, the fluorination agent is formed by addition of hydrogen fluoride to the compound for constituting the hydrogen fluoride containing composition of the invention. Successively, a compound to be reacted can be added to the resulting fluorination agent and the fluorine exchange reaction can be carried out. That is, the composition can be formed by adding hydrogen fluoride to the compound which is liquid in the standard state (25° C., 1 atmosphere) and has a boiling point of 120° C. or more, or to the compound which is liquid in the standard state (25° C., 1 atmosphere) and has a boiling point of 120° C. or more and pka of 12 or more at 25° C., the compound to be fluorinated is charged to the resulting composition, and the fluorination reaction can be carried out.

In the reaction, anhydrous hydrogen fluoride is usually added in such a velocity that short pass of anhydrous hydrogen fluoride does not occur and violent exotherm is not accompanied.

For example, when the addition amount of anhydrous hydrogen fluoride is appropriately 100 g for 50 g of the compound which constitutes the hydrogen fluoride containing composition, the addition velocity is usually 1.5 to 3.0 g/min, preferably 2.0 to 2.5 g/min. However, exotherm is great at the initiation time of anhydrous hydrogen fluoride addition and thus slow down of addition velocity is required.

The addition temperature of anhydrous hydrogen fluoride depends upon the reactivity of the solvent and reaction substrate and is in the range of preferably −40 to 100° C., more preferably −20 to 90° C. in view of the reaction velocity of a successive fluorinating reaction and stability of the fluorination agent.

The fluorine compound formed by the fluorinating reaction using the fluorination agent of the invention can be isolated with ease from the reaction mixture by way of extraction, recrystallization or distillation.

After the reaction, the fluorination agent can be recovered consumed amount of hydrogen fluoride is supplemented to the recovered fluorination agent, and the resulting reactivated agent can be used again.

EXAMPLE

The invention will hereinafter be illustrated further in detail by way of examples. However, these examples are not to be consumed to limit the scope of the invention. The concentration of 1,3-dimethyl-2-imidazolidinone (DMi) in Example 1 was measured by gas chromatography.

The concentration of fluorine ion was measured by absorptiometry using an alizarin complexon reagent.

n in DMi.nHF illustrates the molar number of HF for 1 mole of DMi (shall be the same for other compounds).

Example 1

Synthesis of DMi.nHF

To a polyethylene vessel equipped with a Teflon exhaust line, 85.61 g (0.750 mol) of DMi was charged, stirred with cooling to 0 to 5° C., and bubbled 246.12 g (12.300 mol) of anhydrous hydrogen fluoride gas (HF) over 100 minutes as a mixture with nitrogen to prepare DMi.nHF (n=16.4).

The resulting DMi.nHF (n=16.4) was successively maintained at 35° C. with stirring for 2 hours to release 1.50 g (0.075 mol) of HF from the reaction system. Equilibrium of DMi.nHF was thus obtained at n=16.3.

Successively, the reaction mass was stirred at 50° C. for 3 hours to liberate 85.54 g (4.275 mol) of HF out of the reaction system. Equilibrium of DMi.nHF was obtained at n=10.6. Thereafter the resulting reaction mass was stirred at 80° C. for 6 hours to release 70.54 g (3.525 mol) of HF out of the reaction system. Equilibrium of DMi.nHF was obtained at n=5.9.

Further, the resulting reaction mass was stirred at 100° C. for 6 hours to liberate 30.02 g (1.500 mol) of HF out of the reaction system. Equilibrium of DMi.nHF was obtained at n=3.9.

DMi.nHF (n=10.6) was hydrolyzed with alkali and following analytical values were obtained.

|  | DMi(wt %) | HF(wt %) |
|---|---|---|
| Calculated | 35.0 | 65.0 |
| Found | 34.4 | 63.3 |

$^{13}$C-NMR (δ, ppm, neat, DMSO d6 reference): 30.4 (s, CH$_3$), 45.4 (s, CH$_2$), 157.2 (s,c=0), IR(neat) cm$^{-1}$: 1653, 1525, 1457, 1427, 1296, 1252, 1036, 771.

Example 2
Synthesis of TMU.nHF

To a polyethylene vessel equipped with a Teflon exhaust line, 80.50 g (0.693 mole) of 1,1,3,3-tetramethylurea was charged, stirred with cooling to 0 to 5° C., and bubbled 269.01 g (13.444 mol) of anhydrous hydrogen fluoride gas (HF) over 130 minutes as a mixture with nitrogen to prepare TMU.nHF (n=19.4).

The resulting TMU.nHF (n=19.4) was successively maintained at 35° C. with stirring for 6 hours to release 4.16 g (0.208 mol) of HF from the reaction system. Equilibrium of TMU.nHF was obtained at n=19.1.

Thereafter, TMU.nHF (n=19.1) thus obtained was stirred at 50° C. for 6 hours to liberate 99.83 g (4.989 mol) of HF out of the reaction system. Equilibrium of TMU.nHF was obtained at n=11.9.

Example 3
Synthesis of DBi.nHF

To a polyethylene vessel equipped with a Teflon exhaust line, 60.39 g (0.305 mole) of 1,3-di-n-butyl-2-imidazolidinone (DBi) was charged, stirred with cooling to 0 to 5° C., and bubbled 96.43 g (4.819 mol) of anhydrous hydrogen fluoride gas (HF) over 90 minutes as a mixture with nitrogen to prepare DBi-nHF (n=15.8).

Successively, the resulting DBi.nHF (n=15.8) was stirred at 35° C. for 6 hours to release 0.60 g (0.030 mol) of HF out of the reaction system. Equilibrium of DBi.nHF was obtained at n=15.7.

Thereafter, DBi.nHF (n=15.7) thus obtained was stirred at 50° C. for 12 hours to liberate 37.24 g (1.861 mol) of HF out of the reaction system. Equilibrium of DBi.nHF was obtained at n=9.6.

Example 4
Synthesis of DMPU.nHF

To a polyethylene vessel equipped with a Teflon exhaust line, 64.09 g (0.500 mol) of N,N'-dimethylpropyleneurea (DMPU) was charged, stirred with cooling to 0 to 5° C., and bubbled 199.82 g (9.986 mol) of anhydrous hydrogen fluoride gas (HF) over 80 minutes as a mixture with nitrogen to prepare DMPU.nHF (n=20.0).

Successively, thus obtained DMPU.nHF (n=20.0) was stirred at 35° C. for 4 hours to release 0.72 g (0.036 mol) of HF out of the reaction system. Equilibrium of DMPU.nHF was obtained at n=19.9.

Thereafter, the resulting DMPU.nHF (n=19.9) was stirred at 50° C. for 6 hours to liberate 72.04 g (3.600 mol) of HF out of the reaction system. Equilibrium of DMPU.nHF was obtained at n=12.7.

Further, DMPU.nHF (n=12.7) thus obtained was stirred at 80° C. for 5 hours to release 61.03 g (3.050 mol) of HF out of the reaction system. Equilibrium of DMPU.nHF was obtained at n=6.6.

Moreover, the resultant DMPU.nHF (n=6.6) was stirred at 100° C. for 5 hours to release 12.01 g (0.600 mol) of HF out of the reaction system. Equilibrium of DMPU.nHF was obtained at n=5.4.

Example 5
Synthesis of DMF.nHF

To a polyethylene vessel equipped with a Teflon exhaust line, 73.10 g (1.000 mole) of N,N'-dimethylformamide (DMF) was charged, stirred with cooling to 0 to 5° C., and bubbled 380.19 g (19.000 mol) of anhydrous hydrogen fluoride gas (HF) over 150 minutes as a mixture with nitrogen to prepare DMF.nHF (n=19.0).

Successively, the resulting DMF.nHF (n=19.0) was stirred at 35° C. for 4 hours to release 8.00 g (0.400 mol) of HF out of the reaction system. Equilibrium of DMF.nHF was obtained at n=18.6.

Thereafter, thus obtained DMF.nHF (n=18.6) was stirred at 50° C. for 5 hours to liberate 166.08 g (8.300 mol) of HF out of the reaction system. Equilibrium of DMF.nHF was obtained at n=10.3.

Further, the resultant DMF.nHF was stirred at 80° C. for 5 hours to release 98.05 g (4.900 mol) of HF out of the reaction system. Equilibrium of DMF.nHF was obtained at n=5.4.

Moreover, DMF.nHF (n=5.4) thus obtained was stirred at 100° C. for 4 hours to liberate 16.01 g (0.800 mol) of HF out of the reaction system. Equilibrium of DMF.nHF was obtained at n=4.6.

Example 6
Synthesis of DMAC.nHF

To a polyethylene vessel equipped with a Teflon exhaust line, 43.56 g (0.500 mole) of N,N-dimethylacetamide (DMAC) was charged, stirred with cooling to 0 to 5° C., and bubbled 203.10 g (10.150 mol) of anhydrous hydrogen fluoride gas (HF) over 80 minutes as a mixture with nitrogen to prepare DMAC.nHF (n=20.3).

Successively, DMAC.nHF (n=20.3) thus obtained was stirred at 35° C. for 6 hours to release 1.00 g (0.050 mol) of HF out of the reaction system. Equilibrium of DMAC.nHF was obtained at n=20.2.

Thereafter, the resultant DMAC.nHF (n=20.2) was stirred at 50° C. for 6 hours to liberate 81.04 g (4.050 mol) of HF out of the reaction system. Equilibrium of DMAC.nHF was obtained at n=12.1.

Further, DMAC.nHF (n=12.1) thus obtained was stirred at 80° C. for 5 hours to liberate 59.03 g (2.950 mol) of HF out of the reaction system. Equilibrium of DMAC.nHF was obtained at n=6.2.

Moreover, the resultant DMAC.nHF (n=6.2) thus obtained was stirred at 100° C. for 5 hours to release 13.01 g (0.650 mol) of HF out of the reaction system. Equilibrium of DMAC.nHF was obtained at n=4.9.

Example 7
Synthesis of NMP.nHF

To a polyethylene vessel equipped with a Teflon exhaust line, 49.57 g (0.500 mol) of 1-methyl-2-pyrrolidinone (NMP) was charged, stirred with cooling to 0 to 5° C., and bubbled 208.10 g (10.400 mol) of anhydrous hydrogen fluoride gas (HF) over 90 minutes as a mixture with nitrogen to prepare NMP.nHF (n=20.8).

Successively, thus obtained NMP.nHF (n=20.8) was stirred at 35° C. for 6 hours to release 4.00 g (0.200 mol) of HF out of the reaction system. Equilibrium of NMP.nHF was obtained at n=20.4.

Thereafter, the resultant NMP.nHF (n=20.4) was stirred at 50° C. for 6 hours to liberate 79.04 g (3.950 mol) of HF out of the reaction system. Equilibrium of NMP.nHF was obtained at n=12.5.

Further, NMP.nHF (n=12.5) thus obtained was stirred at 80° C. for 5 hours to release 66.03 g (3.300 mol) of HF out of the reaction system. Equilibrium of NMP.nHF was obtained at n=5.9.

Moreover, the resulting NMP.nHF (n=5.9) was stirred at 100° C. for 6 hours to liberate 16.01 g (0.800 mol) of HF out of the reaction system. Equilibrium of NMP.nHF was obtained at n=4.3.

Example 8
Synthesis of diethylene glycol dimethyl ether.nHF

To a polyethylene vessel equipped with a Teflon exhaust line, 67.09 g (0.500 mole) of diethylene glycol dimethyl ether (Diglyme) was charged, stirred with cooling to 0 to 5° C., and bubbled 199.10 g (9.950 mol) of anhydrous hydrogen fluoride gas (HF) over 80 minutes as a mixture with nitrogen to prepare-Diglyme.nHF (n=19.9).

Successively, Diglyme.nHF (n=19.9) thus obtained was stirred at 35° C. for 4 hours to release 2.00 g (0.100 mol) of HF out of the reaction system. Equilibrium of Diglyme.nHF was obtained at n=19.7.

Thereafter, the resultant Diglyme.nHF (n=19.7) was stirred at 50° C. for 6 hours to liberate 78.04 g (3.900 mol) of HF out of the reaction system. Equilibrium of Diglyme.nHF was obtained at n=11.9.

Moreover, thus obtained Diglyme.nHF (n=11.9) stirred at 80° C. for 5 hours to release 75.04 g (3.750 mol) of HF out of the reaction system. Equilibrium of Diglyme.nHF was obtained at n=4.4.

Further, the resultant Diglyme.nHF (n=4.4) was stirred at 100° C. for 4 hours to liberate 33.02 g (1.650 mol) of HF out of the reaction system. Equilibrium of Diglyme.nHF was obtained at n=1.1.

Example 9
Synthesis of n-butyl acetate.nHF

To a polyethylene vessel equipped with a Teflon exhaust line, 24.97 g (0.215 mole) of n-butyl acetate (AcOnBu) was charged, stirred with cooling to 0 to 5° C., and bubbled 84.76 g (4.236 mol) of anhydrous hydrogen fluoride gas (HF) over 50 minutes as a mixture with nitrogen to prepare AcOnBu.nHF (n=19.7).

Successively, thus obtained AcOnBu.nHF (n=19.7) was stirred at 35° C. for 5 hours to release 26.25 g (1.312 mol) of HF out of the reaction system. Equilibrium of AcOnBu.nHF was obtained at n=13.6.

Thereafter, the resulting AcOnBu.nHF (n=13.6) was stirred at 50° C. for 5 hours to liberate 38.72 g (1.935 mol) of HF out of the reaction system. Equilibrium of AcOnBu.nHF was obtained at n=4.6.

Further, AcOnBu.nHF (n=4.6) thus obtained was stirred at 80° C. for 4 hours to liberate 13.77 g (0.688 mol) of HF out of the reaction system. Equilibrium of AcOnBu.nHF was obtained at n=1.4.

Moreover, the resultant AcOnBu.nHF (n=1.4) was stirred at 100° C. for 3 hours to release 2.16 g (0.108 mol) of HF out of the reaction system. Equilibrium of AcOnBu.nHF was obtained at n=0.9.

Example 10
Synthesis of HMPA.nHF

To a polyethylene vessel equipped with a Teflon exhaust line, 30.46 g (0.170 mol) of hexamethylphosphoramide (HMPA) was charged, stirred with cooling, and bubbled 67.69 g (3.383 mol) of anhydrous hydrogen fluoride gas (HF) over 50 minutes as a mixture with nitrogen to prepare HMPA.nHF (n=19.9).

Successively, thus obtained HMPA.nHF (n=19.9) was stirred at 35° C. for 3 hours. However, no liberation of HF was found.

Thereafter, the composition was stirred at 50° C. for 5 hours to release 0.34 g (0.017 mol) of HF out of the reaction system. Equilibrium of HMPA.nHF was obtained at n=19.8.

Further, HMPA.nHF (n=19.8) thus obtained was heated at 80° C. for 4 hours to liberate 1.70 g (0.085 mol) of HF out of the reaction system. Equilibrium of HMPA.nHF was obtained at n=19.3.

Moreover, the resulting HMPA.nHF (n=19.3) was stirred at 100° C. for 4 hours to release 3.74 g (0.187 mol) of HF out of the reaction system. Equilibrium of HMPA.nHF was obtained at n=18.2.

Example 11
Synthesis of benzotrifluoride

To a polyethylene vessel equipped with a Teflon exhaust line which was cooled to −15° C., 8.89 g (327.5 m mol as HF) of DMi.16HF and 3.99 g (20.4 m mol) of benzotrichloride were charged, and reacted at 30° C. for 6 hours. After finishing the reaction, the reaction mixture was analyzed by gas chromatography. As a result, the conversion ratio of benzotrichloride was 100%, the yield of benzotrifluoride was 77.2%, and the yield of (chlorodifluoromethyl)benzene was 22.8%. The reaction mixture was successively reacted at 50° C. for 6 hours. Benzotrifluoride was obtained in the yield of 99.8%.

Example 12
Synthesis of benzotrifluoride

To a polyethylene vessel equipped with a Teflon exhaust line which was cooled to −15° C., 10.08 g (327.5 m mol as HF) of DMi.10.6HF and 2.31 g (11.8 m mol) of benzotrichloride were charged and reacted at 50° C. for 6 hours. After finishing the reaction, the reaction mixture was analyzed by gas chromatography. As a result, the conversion ratio of benzotrichloride was 100%, the yield of benzotrifluoride was 87.4%, and the yield of (chlorodifluoromethyl)benzene was 12.6%.

Example 13
Synthesis of (chlrordifluoromethyl)benzene

To a polyethylene vessel equipped with a Teflon exhaust line which was cooled to −15° C., 75.2 g (2.795 mol as HF) of DMi.16.4HF and 127.1 g (0.650 mol) of benzotrichloride were charged, and reacted at 30° C. for 10 hours. After finishing the reaction, the reaction mixture was analyzed by gas chromatography. As a result, the conversion ratio of benzotrichloride was 95.0%, the yield of benzotrifluoride was 4.7%, the yield of (chlorodifluoromethyl)benzene was 65.9% and the yield of (dichlorofluoromethyl)benzene was 24.4%.

Example 14
Synthesis of (dichlorofluoromethyl)benzene

To a polyethylene vessel equipped with a Teflon exhaust line which was cooled to −15° C., 80.3 g (104.4 m mol as HF) of DMi.2HF and 4.79 g (24.5 m mol) of benzotrichloride were charged and reacted at 80° C. for 36 hours. After finishing the reaction, the reaction mixture was analyzed by gas chromatography. As a result, the conversion ratio of benzotrichloride was 77.6%, the yield of (chlorodifluoromethyl)benzene was 10.6%, and the yield of (dichlorofluoromethyl)benzene was 67.0%.

Example 15
Synthesis of (trifluoromethoxy)benzene

To a Teflon internal of a SUS sealed container, 1.00 g (4.7 in mol) of (trichloromethoxy)benzene and 2.04 g (75.2 m mol as HF) of DMi-16HF were charged and stirred at 120° C. for 3 hours. After finishing the reaction, the reaction mixture was neutralized with a saturated aqueous sodium hydrogen carbonate solution and extracted with 50 ml of methylene chloride. The extracted organic layer was washed twice with 100 ml of water, and dried over anhydrous sodium sulfate. After drying, anhydrous sodium sulfate was filtered off and filtrate was analyzed by gas chromatography. As a result, the conversion ratio of (trichloromethoxy) benzene was 100% and the yield of (trifluoromethoxy) benzene was 99.8%.

Example 16
Synthesis of benzotrifluoride

To a polyethylene vessel equipped with a Teflon exhaust line which was cooled to −15° C., 8.96 g (320.0 m mol as HF) of DMPU.16HF and 3.91 g (20.0 m mol) of benzotrichloride were charged and reacted at 30° C. for 6 hours and 50° C. for 6 hours. After finishing the reaction, the reaction mixture was analyzed by gas chromatography. As a result, the conversion ratio of benzotrichloride was 100%, the yield of benzotrifluoride was 98.5%, and the yield of (chlorodifluoromethyl)benzene was 1.5%.

Example 17
Synthesis of benzotrifluoride

To a polyethylene vessel equipped with a Teflon exhaust line which was cooled to −15° C., 7.86 g (320.0 m mol as HF) of DMF.16HF and 3.93 g (20.1 m mol) of benzotrichloride were charged and reacted at 30° C. for 6 hours and 50° C. for 6 hours After finishing the reaction, the reaction mixture was analyzed by gas chromatography. As a result, the conversion ratio of benzotrichloride was 100%, the yield of benzotrifluoride was 99.8%.

Example 18
Synthesis of benzotrifluoride

To a polyethylene vessel equipped with a Teflon exhaust line which was cooled to −15° C., 18.62 g (655.7 m mol as HF) of Diglyme.16HF and 7.94 g (40.6 m mol) of benzotrichloride were charged, and reacted at 30° C. for 6 hours and 50° C. for 6 hours After finishing the reaction, the reaction mixture was analyzed by gas chromatography. As a result, the conversion ratio of benzotrichloride was 100%, the yield of benzotrifluoride was 96.7%, and the yield of (chlorodifluoromethyl)benzene was 3.3%.

Example 19
Synthesis of benzotrifluoride

To a polyethylene vessel equipped with a Teflon exhaust line which was cooled to −15° C., 8.07 g (295.9 m mol as HF) of AcOnBu.16HF and 3.62 g (18.5 m mol) of benzotrichloride were charged, and reacted at 30° C. for 6 hours and 50° C. for 6 hours. After finishing the reaction, the reaction mixture was analyzed by gas chromatography. As a result, the conversion ratio of benzotrichloride was 100% and the yield of benzotrifluoride was 99.8%.

Example 20
Synthesis of benzotrifluoride

To a polyethylene vessel equipped with a Teflon exhaust line which was cooled to −15° C., 8.14 g (280.6 m mol as HF) of HMPA.19.9HF and 3.44 g (17.6 m mol) of benzotrichloride were charged and reacted at 30° C. for 6 hours and at 50° C. for 6 hours After finishing the reaction, the reaction mixture was analyzed by gas chromatography. As a result, the conversion ratio of benzotrichloride was 89.4%, the yield of benzotrifluoride was 5.2%, the yield of (chlorodifluoromethyl)benzene was 59.0% and the yield of (dichlorofluoromethyl)benzene was 25.2%.

Example 21
Synthesis of 4-chloro-3,5-bis(trifluoromethyl)pyrazole

To an internal Teflon vessel of SUS sealed container, 25.43 g (959.93 m mol as HF) of DMi-17.6HF and 4-chloro-3,5-bis(trichloromethyl) pyrazole were charged and heated in an oil bath at 140° C. for 16 hours with electromagnetic stirring to carry out a halogen exchange reaction. After finishing the reaction, the reaction mixture was analyzed by GC-MS. As a result, disappearance of the raw material peak and formation of a peak of the mass number 238 were confirmed. The reaction mixture was extracted with diethyl ether, the solvent was removed, and the remained yellow brown oil was distilled to obtain a colorless crystal was analyzed to identify 4-chloro-3,5-bis(trifluoromethyl) pyrazole.

Elemental analyses (wet %)

|  | F | Cl | C | H | N |
| --- | --- | --- | --- | --- | --- |
| Calculated (wt %) | 47.79 | 14.86 | 25.18 | 0.42 | 11.75 |
| Found (wt %) | 46.5 | 14.46 | 26.11 | 0.69 | 12.24 |

$^{13}$C-NMR (δ, ppm, CDCl$_3$ solvent, CDCl$_3$ reference, 25° C.); 109.7, 115.2, 117.9, 120.5, 123.2, 135.5, 135.8, 136.2, 136.6

Coupling constant:

J(C—F): 270.25 Hz

J(C—C—F): 38.61 Hz $^1$H-NMR (δ, ppm, CDCl$_3$, solvent, CDCl$_3$ reference, 25° C.); 8 to 10 (N—H)

Example 22
Synthesis of 2,4-dichloro-5-trifluoromethylpyrimidine

To an internal Teflon vessel of SUS sealed container, 1.0 g (3.8 m mol) of 2,4-dichloro-trichloromethylpyrimidine and 6.0 g (220.8 m mol as HF) of DMi.16HF were charged and stirred at 120° C. for 3 hours. A saturated aqueous sodium hydrogen carbonate solution added to the resulting reaction mixture and analyzed by GC-MS. 2,4-Dichloro-5-trifluoromethylpyrimidine was obtained.

Mass spectrum (EI): m/z=216(M+, 100%), 181(M+-Cl, 70%), 69(CF3+, 46%).

Example 23
Synthesis of ethyl 1-methyl-3-trifluoromethylpyrazole-4-carboxylate To an internal Teflon vessel of SUS sealed container, 4.0 g (14.7 m mol) of ethyl 1-methyl-3-trichloromethylpyrazole-4-carboxylate and 0.4 g (235 m mol as HF) were charged and stirred at 120° C. for 19 hours. The reaction mixture was neutralized with 200 ml of saturated aqueous sodium hydrogen carbonate solution and extracted with 100 ml of ethyl acetate.

The extracted organic layer was washed twice with 100 ml of water and dried over 10 g of anhydrous sodium sulfate. After drying, anhydrous sodium was filtered off and the filtrate was concentrated under reduced pressure to obtain 32 g (14.4 m mol) of ethyl 1-methyl-3-trifluoromethylpyrazole-4-carboxylate as a yellow crystal. The yield was 98%.

Melting point: 61.5 to 63.1° C.

$^1$H-NMR (CDCl$_3$/TMS; δ ppm) : 1.35 (3H, t, J=7.0 Hz, 3.97 (3H, s), 4.30 (2H, q, J=7.0 Hz), 7.95 (1H s), Mass spectrum: 223 (M$^+$).

POSSIBILITY FOR USE IN INDUSTRY

The hydrogen fluoride containing composition of the invention is safe, can be handled with ease, and serves a useful function as a fluorination agent having similar reactivity to hydrogen fluoride and other chemical reagents. The improved type HF-like fluorination agent is extremely useful for production of fluorine containing composition in industry.

That is, on applying the composition to a fluorination agent in industry, the composition does not require specific equipment or technique and can be used with safety and ease.

Conventionally, various fluorination agents have been developed in order to prepare fluorine-containing compounds.

However, these conventional fluorination agents have problems in industry due to specific factors. On the other hand, the fluorination agent of the invention can be used in industry as a fluorination agent which can preclude these problems and thus has extremely great possibility for industrial utilization.

What is claimed is:

1. A hydrogen fluoride containing composition comprising hydrogen fluoride and a compound which is liquid in the standard state (25° C., 1 atmosphere) and has a boiling point of 120° C. or more wherein the compound is represented by formula (3):

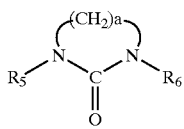
(3)

wherein a is an integer of 2 to 3, and R$_5$ and R$_6$ are a substituted or unsubstituted alkyl group having 1 to 6 carbon atoms and can be the same or different.

2. A hydrogen fluoride containing composition according to claim 1 wherein the composition comprises hydrogen fluoride and the compound having the formula (4):

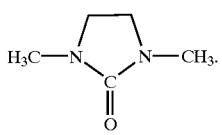
(4)

3. A hydrogen fluoride containing composition according to claim 1 wherein the composition comprises hydrogen fluoride and the compound having the formula (5):

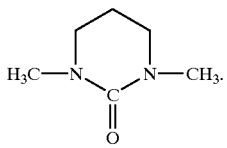
(5)

4. A hydrogen fluoride containing composition according to claim 1 wherein the composition comprises hydrogen fluoride and the compound having the formula (9):

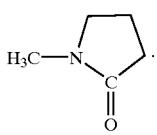
(9)

5. A preparation process comprising reacting the hydrogen fluoride containing composition according to any one of claims 1, 2, 3 and 4, with a compound represented by the formula (15):

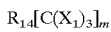
R$_{14}$[C(X$_1$)$_3$]$_m$ (15)

wherein R$_{14}$ is a substituted or unsubstituted alkyl, alkoxy, aryl or aryloxy group, and X$_1$ is a hydrogen, fluorine, chlorine, bromine or iodine atom and can be the same or different except three X$_1$ are not simultaneously hydrogen or fluorine atom and three X$_1$ do not consist of hydrogen and fluorine atom alone, and m is an integer of 1 to 6, to obtain a fluorine compound represented by the formula (16):

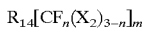
R$_{14}$[CF$_n$(X$_2$)$_{3-n}$]$_m$ (16)

wherein R$_{14}$ is a substituted or unsubstituted alkyl, alkoxy, aryl or alkoxy group, and X$_2$ is a hydrogen, chlorine, bromine or iodine atom and can be the same or different, and n is an integer of 1 to 3 and n is an integer 1 to 6.

6. A preparation process of a fluorine containing heterocyclic aromatic compound comprising reacting the hydrogen fluoride containing composition according to any one of claims 1, 2, 3 and 4, with a heterocyclic aromatic compound represented by the formula (17):

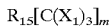
R$_{15}$[C(X$_1$)$_3$]$_m$ (17)

wherein R$_{15}$ is a substituted or unsubstituted heterocyclic aromatic group, and X$_1$ is a hydrogen, fluorine, chlorine, bromine or iodine atom and can be the same or different except three X$_1$ are not simultaneously hydrogen or fluorine atoms and three X$_1$ do not consist of hydrogen and fluorine atom alone, and m is an integer of 1 to 9, to obtain a fluorine containing heterocyclic aromatic compound represented by the formula (18):

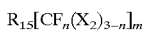
R$_{15}$[CF$_n$(X$_2$)$_{3-n}$]$_m$ (18)

wherein R$_{15}$ is a substituted or unsubstituted heterocyclic aromatic group, and X$_1$ is a hydrogen, fluorine, chlorine, bromine or iodine atom and can be the same or different, and n is an integer of 1 to 3 and m is an integer of 1 to 9.

7. A preparation process of a fluorine containing heterocyclic aromatic compound according to claim 6 wherein the heterocyclic aromatic compound represented by the formula (17) is a cyclic compound having 1 to 4 elements of one or more species selected from the group consisting of nitrogen, oxygen and sulfur.

8. A preparation process of a fluorine containing heterocyclic aromatic compound according to claim 6 wherein the heterocyclic aromatic compound represented by the formula (17) is a heterocyclic aromatic compound having a ring selected from furan, thiophene, pyrrole, pyrazole, imidazole, isoxazole, thiazole, thiadiazole, pyridine, pyridazine, pyrimidine, pyrazine, triazine, benzofurane, indole, thianaphthene, benzimidazole, benzoxazole, benzothiazole, benzotriazole, purine, quinoline, isoquinoline, cinnoline, quinoxaline, dibenzothiophene, acridine and phenanthroline.

9. A preparation process of a fluorine containing heterocyclic aromatic compound according to claim 6 wherein the heterocyclic aromatic compound represented by the formula (17) is a compound represented by the formula (19):

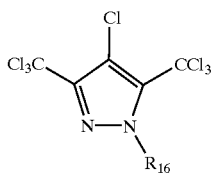

(19)

wherein $R_{16}$ is a hydrogen atom or an alkyl group having 1 to 4 carbon atoms.

10. A preparation process of a fluorine containing heterocyclic aromatic compound according to claim 6 wherein the heterocyclic aromatic compound represented by the formula (17) is 4-chloro-3,5-bis(trichloromethyl) pyrazole having the formula (20):

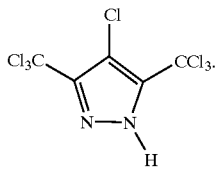

(20)

11. A preparation process of a fluorine containing heterocyclic aromatic compound according to claim 6 wherein the heterocyclic aromatic compound represented by the formula (17) is a compound represented by the formula (21):

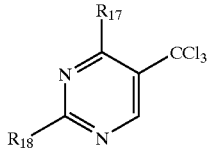

(21)

wherein $R_{17}$ and $R_{18}$ are a hydrogen, chlorine, fluorine atom, a hydroxyl, alkyl having 1 to 4 carbon atoms, alkoxy, aryl or aryloxy group, and can be the same or different.

12. A preparation process of a fluorine containing heterocyclic aromatic compound according to claim 6 wherein the heterocyclic aromatic compound represented by the formula (17) is 2,4-dichloro-5-trichloromethylpyrimidine having the formula (22):

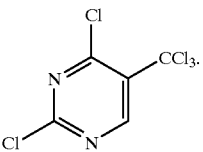

(22)

13. A preparation process of a fluorine containing heterocyclic aromatic compound according to claim 6 wherein the heterocyclic aromatic compound represented by the formula (17) is a compound represented by the formula (23):

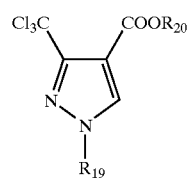

(23)

wherein $R_{19}$ and $R_{20}$ are a hydrogen atom or alkyl group having 1 to 4 carbon atoms, and can be the same or different.

14. A preparation process of a fluorine containing heterocyclic aromatic compound according to claim 1 wherein the heterocyclic aromatic compound represented by the formula (17) is ethyl 1-methyl-3-trichloromethylpyrazole 4-carboxylate having the formula (24):

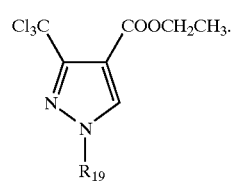

(24)

15. A preparation process of a fluorine compound according to claim 5, wherein the hydrogen fluoride containing composition comprises hydrogen fluoride and the compound represented by the formula (4):

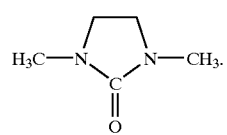

(4)

16. A preparation process of a fluorine containing heterocyclic aromatic compound to claim 6, wherein the hydrogen fluoride containing composition comprises hydrogen fluoride and the compound represented by the formula (4):

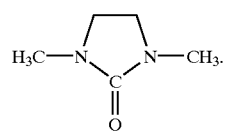

(4)

17. A preparation process of a fluorine containing heterocyclic aromatic compound to claim 7, wherein the hydrogen fluoride containing composition comprises hydrogen fluoride and the compound represented by the formula (4):

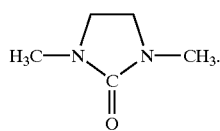

(4)

18. A preparation process of a fluorine containing heterocyclic aromatic compound to claim 8, wherein the hydrogen fluoride containing composition comprises hydrogen fluoride and the compound represented by the formula (4):

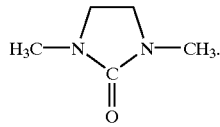

(4)

19. A preparation process of a fluorine containing heterocyclic aromatic compound to claim 9, wherein the hydrogen fluoride containing composition comprises hydrogen fluoride and the compound represented by the formula (4):

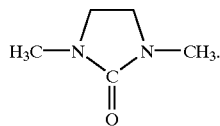

(4)

20. A preparation process of a fluorine containing heterocyclic aromatic compound to claim 10, wherein the hydrogen fluoride containing composition comprises hydrogen fluoride and the compound represented by the formula (4):

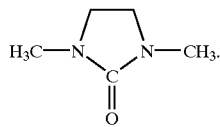

(4)

21. A preparation process of a fluorine containing heterocyclic aromatic compound to claim 11, wherein the hydrogen fluoride containing composition comprises hydrogen fluoride and the compound represented by the formula (4):

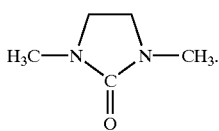

(4)

22. A preparation process of a fluorine containing heterocyclic aromatic compound to claim 12, wherein the hydrogen fluoride containing composition comprises hydrogen fluoride and the compound represented by the formula (4):

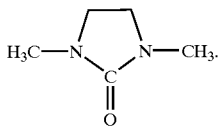

(4)

23. A preparation process of a fluorine containing heterocyclic aromatic compound to claim 13, wherein the hydrogen fluoride containing composition comprises hydrogen fluoride and the compound represented by the formula (4):

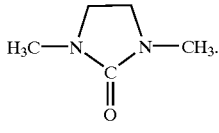

(4)

24. A preparation process of a fluorine containing heterocyclic aromatic compound to claim 14, wherein the hydrogen fluoride containing composition comprises hydrogen fluoride and the compound represented by the formula (4):

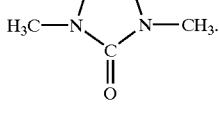

(4)

* * * * *